United States Patent
Berkel et al.

(10) Patent No.: US 10,759,728 B2
(45) Date of Patent: Sep. 1, 2020

(54) PROCESS AND SYSTEM FOR PRODUCING DIMETHYL ETHER

(71) Applicant: Stichting Energieonderzoek Centrum Nederland, Le Petten (NL)

(72) Inventors: Franciscus Petrus Felix Van Berkel, Le Petten (NL); Hendricus Adrianus Johannes Van Dijk, Le Petten (NL); Paul Dean Cobden, Le Petten (NL); Willem Gerrit Haije, Le Petten (NL); Jaap Ferdinand Vente, Le Petten (NL)

(73) Assignee: NEDERLANDSE ORGANISATIE VOOR TOEGEPAST-NATUURWETEN SCHAPPELIJK ONDERZOEK TNO, 'S-Gravenhage (NL)

( * ) Notice: Subject to any disclaimer, the term of this patent is extended or adjusted under 35 U.S.C. 154(b) by 0 days.

(21) Appl. No.: 16/069,145

(22) PCT Filed: Jan. 12, 2017

(86) PCT No.: PCT/EP2017/050593
§ 371 (c)(1),
(2) Date: Jul. 10, 2018

(87) PCT Pub. No.: WO2017/121817
PCT Pub. Date: Jul. 20, 2017

(65) Prior Publication Data
US 2019/0016656 A1   Jan. 17, 2019

(30) Foreign Application Priority Data
Jan. 12, 2016 (NL) ..................................... 2016084

(51) Int. Cl.
*C07C 41/01* (2006.01)
*C01B 3/02* (2006.01)
(Continued)

(52) U.S. Cl.
CPC ............ *C07C 41/01* (2013.01); *B01D 53/261* (2013.01); *B01D 53/268* (2013.01); *B01J 8/0492* (2013.01);
(Continued)

(58) Field of Classification Search
CPC ..... C07C 43/043; C07C 41/01; Y02P 20/582; Y02P 20/146; C01B 3/02;
(Continued)

(56) References Cited

U.S. PATENT DOCUMENTS

2016/0115405 A1* 4/2016 Zubrin ....................... C10J 3/34
205/628

FOREIGN PATENT DOCUMENTS

| EP | 0737648 | 10/1996 |
| WO | WO-2005/026093 | 3/2005 |
| WO | WO-2007/081212 | 7/2007 |

OTHER PUBLICATIONS

Azizi et al., "Dimethyl ether; A review of technologies and production challenges", Chemical Engineering and Processing: Process Intensification, 2014, 82:150-172.
(Continued)

*Primary Examiner* — Jafar F Parsa
(74) *Attorney, Agent, or Firm* — Foley & Lardner LLP (57) ABSTRACT

The invention relates to an improved process and system for the synthesis of dimethyl ether (DME) from a feedstock comprising $H_2$ and $CO_x$, wherein x=1-2. The process according to the invention comprises (a) subjecting the gaseous mixture comprising synthesis gas originating from step (c) to DME synthesis by contacting it with a catalyst capable of converting synthesis gas to DME to obtain a gaseous mixture comprising DME; (b) subjecting a gaseous mixture comprising the gaseous mixture originating from step (a) to a separation-enhanced reverse water gas shift reaction; and
(Continued)

(c) subjecting the gaseous mixture originating from step (b) to DME/synthesis gas separation to obtain DME and a gaseous mixture comprising synthesis gas, which is recycled to step (a). Herein, the feedstock is introduced in step (a) or step (b) and the molar ratio of $H_2$ to $CO_x$ in the gaseous mixture which is subjected to step (b) is at least (x+0.8). Also a system for performing the reaction according to the invention is disclosed.

15 Claims, 1 Drawing Sheet (51) Int. Cl.
*B01D 53/26* (2006.01)
*B01J 8/04* (2006.01)
*B01J 19/24* (2006.01)

(52) U.S. Cl.
CPC .............. *B01J 19/245* (2013.01); *C01B 3/02* (2013.01); *B01J 2208/00628* (2013.01); *C01B 2203/0283* (2013.01); *Y02P 20/146* (2015.11); *Y02P 20/582* (2015.11)

(58) Field of Classification Search
CPC ........ C01B 2203/0283; C01B 2203/06; B01D 53/268; B01D 53/261; B01J 19/245; B01J 8/0492; B01J 53/268; B01J 2208/00628; B01J 20/2808; B01J 20/165
See application file for complete search history.

(56) References Cited

OTHER PUBLICATIONS

Hamidi et al., "Dimethyl ether synthesis in a gas-solid-solid trickle flow reactor with continuous adsorbent regeneration", Journal of the Taiwan Institute of Chemical Engineers, 2015, 47:105-112.

Iliuta et al., "Sorption-enhanceddimethylethersynthesis—Multiscale reactormodeling", Chemical Engineering Science, 2011, 66:2241-2251.

Ogawa et al., "Direct Dimethyl Ether Synthesis", Journal of Natural Gas Chemistry, 2003, 12(4):219-227.

PCT International Search Report and Written Opinion for Application No. PCT/EP2017/050593 dated Mar. 17, 2017. (12 pages).

Peng et al., "Single-Step Syngas-to-Dimethyl Ether Processes for Optimal Productivity, Minimal Emissions, and Natural Gas-Derived Syngas", Ind. Eng. Chem. Res., 1999, 38(11):4381-4388.

Ressler, S., et al., "Reactive gas adsorption", in Integrated Reaction and Separation Operations: Modelling and experimental validation, eds. H. Schmidt-Traub, et al., 2006, pp. 149-190, Springer-Verlag Berlin Heidelberg.

\* cited by examiner

FIG. 1

PROCESS AND SYSTEM FOR PRODUCING DIMETHYL ETHER

CROSS-REFERENCE TO RELATED APPLICATIONS

This application is a U.S. national stage application of International Patent Application No. PCT/EP2017/050593, filed on Jan. 12, 2017, which claims priority to the Netherlands Application No. 2016084, filed on Jan. 12, 2016, the content of each of these applications is incorporated herein in its entirety by reference.

The present invention relates to the production of dimethyl ether (DME), in particular to a process and a system for the production of DME.

BACKGROUND

Dimethyl ether (DME) is a valuable compound useful in the chemical industry, e.g. as precursor of dimethyl sulphate, acetic acid or for olefin production. It is an important research chemical and is used as refrigerant and propellant. Moreover, DME may find more widespread use in the future, as it is being developed as novel fuel, e.g. as replacement for or additive to propane in LPG and as diesel fuel additive. It can be produced by catalytic dehydration of methanol, and the methanol can be produced by catalytic hydrogenation of CO or $CO_2$, e.g. using synthesis gas. The production of DME from synthesis gas may thus be accomplished via the direct or the indirect method. The indirect method involves contacting the synthesis gas with a methanol synthesis catalyst to form methanol, which is subsequently contacted with a dehydration catalyst to form DME. Alternatively, methanol could be used as a starting material which is contacted with a dehydration catalyst without the need of a methanol synthesis catalyst. The direct method involves contacting the synthesis gas with a bifunctional catalyst comprising a methanol synthesis catalyst and a dehydration catalyst, such that isolation and purification of the methanol is not required. Both the direct and the indirect method are presently commercially used for the production of DME.

Several reaction schemes for the synthesis of dimethyl ether have been developed, such as:

Methanol synthesis: $CO_2 + 3H_2 \leftrightarrow CH_3OH + H_2O$    (1)

Water gas shift: $CO + H_2O \leftrightarrow H_2 + CO_2$    (2)

Methanol dehydration: $2CH_3OH \leftrightarrow CH_3OCH_3 + H_2O$    (3)

Overall: $3CO + 3H_2 \leftrightarrow CH_3OCH_3(DME) + CO_2$    (4)

Two alternative overall reactions, based on reactions (1) to (3), for the synthesis of DME from synthesis gas are:

$2CO + 4H_2 \leftrightarrow CH_3OCH_3(DME) + H_2O$    (5)

$2CO_2 + 6H_2 \leftrightarrow CH_3OCH_3(DME) + 3H_2O$    (6)

Typically, a direct DME catalyst system contains a methanol synthesis catalyst that is capable of catalysing reactions (1) and (2), and a dehydratation catalyst that is capable of catalysing reaction (3), although certain materials are known that are active in all three reactions. These latter materials are also referred to as bifunctional catalysts. For optimal carbon selectivity towards DME, it is generally preferable that DME is formed (mostly) via reaction (5) and/or (6). As such, the majority of the carbon atoms in the reactants end up in the desired product, i.e. DME, and not in a by-product such as $CO_2$.

The interplay between the various reactions that together form the DME synthesis, such as between reactions (1)-(3) to give any one of overall reactions (4)-(6), is crucial for satisfactory DME yields, especially since all are equilibrium reactions. The CO to $CO_2$ molar ratio—or in the context of the present invention the value of x in $CO_x$—plays a major role. Typically, small amounts of $CO_2$ can be tolerated in the feedstock. However, since the removal of water by reaction (2) is crucial—after all, water is formed in both reaction (1) and (3) and is a by-product in overall reactions (5) and (6)—the $CO_2$ content in the feedstock should be kept as low as possible. The presence of $CO_2$ in the feedstock favours the reverse water gas shift reaction and thus shifts the equilibrium of reactions (1) and (3) towards the reactants. But even with pure CO as carbon oxide species, currently applied methods for the production of DME suffer from the major drawback that satisfactory yields of DME are only obtainable by use of major recycles. Herein, unreacted starting materials are separated from produced DME and rerouted to the reactor to be contacted again with the catalyst system. $CO_2$ is a significant component of such recycles, but since only small amounts of $CO_2$ can be tolerated by the bifunctional catalyst, it needs to be converted to CO before it can be recycled. Economically unfavourable conversion of $CO_2$ into CO is needed, such as a dry reforming step. The equilibrium mixture also typically contains substantial amounts of methanol, which also need to be recycled to the catalyst in order to obtain an overall DME yield that is satisfactory. Such large recycles hamper the flexibility of the process and increase costs associated with e.g. keeping all reactant streams at the desired temperature and pressure. Moreover, large scale energy-consuming separations (e.g. distillations) are needed to isolated DME from the unreacted reactants and intermediates. WO 2005/026093 disclosed a process for producing DME wherein $CO_2$ is converted into CO by a reverse water gas shift reaction, which process requires unfavourable separation of DME and $CO_2$, as well as a large $CO_2$ cycle. The indirect method for the synthesis of DME suffers from the same equilibria and need for recycles, with the only difference that reactions (1) and (2) take place in a different reaction zone as reaction (3). Hence, there remains a need in the art to increase the yield of DME without the need of major recycles, such that DME production may be more flexible and cost effective.

A further issue is the exothermicity of reactions (1)-(3). As these are all highly exothermic, a lot of heat is produced during DME synthesis. State of the art DME production facilities are able to cope with this heat, e.g. by using actively cooled slurry reactors to absorb the heat. As the indirect method for synthesizing DME distributes the heat formation over more than one reactor, this method is generally better capable to cope with the heat formation. The issues and challenges in state of the art DME synthesis are reviewed by Azizi et al. (*Chem. Eng. Proc.* 82, 2014, 150-172).

The use of an adsorbent which selectively binds water, to force the equilibrium of reactions (1) and (3) towards the products methanol and DME has been suggested by Iliuta et al. (Chemical Engineering Science 66 (2011) 2241-2251) and Hamidi et al. (Journal of the Taiwan Institute of Chemical Engineers 47 (2015) 105-112). Iliuta describes a model study for the use of a catalyst system comprising unspecified catalytic particles and zeolite-4 A as a third active material. Hamidi also reports a theoretical study, wherein a fixed bifunctional catalyst is combined with flowing zeolite-4 A particles which are capable of adsorbing water. Ressler et al. (in *Integrated Reaction and Separation Operations, Modelling and experimental validation*, editors: Henner Schmidt-Traub and Andrzej Gorak, Springer Verlag, 2006, ISBN10 3-540-30148-8, Chapter 4: *Reactive gas adsorption*) discloses a single-reactor DME synthesis starting from synthesis gas, using a 25:25:50 (by volume) combination of a methanol synthesis catalyst ($Cu/ZnO/Al_2O_3$), gamma-alumina and zeolite-3 A. In these disclosures, the catalyst system contains three distinct active materials, wherein the zeolite (3 A or 4 A) is used as a water adsorbent. Using a selective water adsorbent in the synthesis of DME is referred to as sorption-enhanced DME synthesis (SEDMES).

The present invention is concerned with providing a process and system for the production of dimethyl ether in a more efficient and cost-effective way. Most importantly, the need for large $CO_2$ recycles and concurrent $CO_2$-assisted reforming steps is obviated. Also, methanol recycles are kept at a minimum and issues with the exothermicity of the reactions are avoided. Lastly, the presence of $CO_2$ in the equilibrium mixture is suppressed, which avoids the need for cumbersome separation of DME from a mixture comprising significant amounts of $CO_2$ and largely eliminates the $CO_2$ recycle, two of the most costly aspects of conventional DME production.

SUMMARY OF THE INVENTION

The inventors found that by combining conventional or separation-enhanced DME synthesis reactor with a separation-enhanced reverse water gas shift reaction reactor greatly improves the yield of DME and reduces or even eliminates the need of large $CO_2$ recycles. As such, many of the drawback of conventional DME syntheses, as discussed above, are obviated. For example, smaller and fewer recycles compared prior art process for the synthesis of DME greatly reduce the costs of the process and improves its flexibility. Moreover, the process according to the invention provides unprecedented flexibility in feedstock composition, as any (mixture of) carbon oxide species can be used and the amount of hydrogen gas in the feedstock can readily be tuned to optimal DME yield. Especially the possibility of using pure $CO_2$ as carbon oxide species in the feedstock is a great improvement over prior art processes.

In a first aspect, the invention concerns a process for the synthesis of dimethyl ether (DME) from a feedstock comprising $H_2$ and $CO_x$, wherein x=1-2, comprising:
(a) subjecting the gaseous mixture comprising synthesis gas originating from step (c) to DME synthesis by contacting it with a catalyst capable of converting synthesis gas to DME to obtain a gaseous mixture comprising DME;
(b) subjecting a gaseous mixture comprising the gaseous mixture originating from step (a) to a separation-enhanced reverse water gas shift reaction; and
(c) subjecting the gaseous mixture originating from step (b) to DME/synthesis gas separation to obtain DME and a gaseous mixture comprising synthesis gas, which is recycled to step (a),
wherein the feedstock is introduced in step (a) or step (b) and wherein the molar ratio of $H_2$ to $CO_x$ in the gaseous mixture which is subjected to step (b) is at least (x+0.8).

In a second aspect, the invention concerns a system for performing the process according to the first aspect, comprising:
(a) an inlet for receiving a feedstock comprising $H_2$ and $CO_x$, wherein x=1-2,
(b) a reverse water gas shift reaction zone for converting $H_2$ and $CO_x$ to $H_2O$ and CO, comprising an inlet (b1) for receiving a gaseous mixture comprising the gaseous mixture originating from zone (d), wherein the molar ratio of $H_2$ to $CO_x$ in the gaseous mixture which is subjected to step (b) is at least (x+0.8), a catalyst bed (b2) comprising a separation-enhanced reverse water gas shift catalyst system, an outlet (b3) for discharging a gaseous mixture;
(c) a separator comprising an inlet (c1) for receiving the gaseous mixture originating from zone (b), means (c2) for separating the gaseous mixture in DME and a gaseous mixture comprising synthesis gas, an outlet (c3) for discharging the gaseous mixture comprising synthesis gas and an outlet (c4) for discharging DME; and
(d) dimethyl ether production zone, comprising an inlet (d1) for receiving the gaseous mixture comprising synthesis gas originating from separator (c), a catalyst system (d2) capable of converting synthesis gas to dimethyl ether, an outlet (d3) for discharging a gaseous mixture,
wherein inlet (a) is in fluid connection with inlet (b1) or inlet (d1), outlet (b3) is in fluid connection with inlet (c1), outlet (c3) is in fluid connection with inlet (d1), and outlet (d3) is in fluid connection with inlet (b1).

DETAILED DESCRIPTION

The present invention involves a process for producing DME from a feedstock comprising $H_2$ and $CO_x$, wherein x=1-2, as well as a system for performing said process. Whenever reference is made to the process, the same applies to the system if appropriate, and whenever reference is made to the system, the same applies to the process if appropriate, as will be understood by the skilled person.

Process

The process according to the invention is for the synthesis of dimethyl ether (DME) from a feedstock comprising $H_2$ and $CO_x$, and comprises:
(a) subjecting the gaseous mixture comprising synthesis gas originating from step (c) to DME synthesis by contacting it with a catalyst capable of converting synthesis gas to DME to obtain a gaseous mixture comprising DME;
(b) subjecting a gaseous mixture comprising the gaseous mixture originating from step (a) to a separation-enhanced reverse water gas shift reaction; and
(c) subjecting the gaseous mixture originating from step (b) to DME/synthesis gas separation to obtain DME and a gaseous mixture comprising synthesis gas, which is recycled to step (a).

Herein, the feedstock is introduced in step (a) or step (b) and the molar ratio of $H_2$ to $CO_x$ in the gaseous mixture which is subjected to step (b) is at least (x+0.8). In the context of the present invention, "gaseous" means gaseous at the process conditions.

The process operates with a recycle, wherein remaining reactants (synthesis gas) that are removed from the product DME in step (c) are recycled to step (a). DME is mainly formed during step (a), but to a lesser extent may also be formed during step (b). The feedstock is typically in the form of a gaseous mixture. In a first embodiment, the feedstock is first subjected to step (b), together with the gaseous mixture originating from step (a), during which the composition of the combined gaseous mixture typically changes. Depending on the nature of the reverse water gas shift reaction and the composition of the feedstock, some DME may already be formed during step (b). The gaseous mixture originating from step (b) is then subjected to step (c), during which any DME formed during step (b) is, together with the DME present in the gaseous mixture originating from step (a), separated from the remaining gaseous mixture. Step (c) thus affords at least two products, the first being a gaseous mixture comprising synthesis gas and other components originating step (b) and substantially no DME, and the second being DME or a mixture comprising DME. In a second embodiment, the feedstock is first subjected to step (a), together with the recycle from step (c), during which an equilibrium gaseous mixture comprising DME and $CO_2$ is formed. The gaseous mixture originating from step (a) is then subjected to step (b), during which $CO_2$ is converted into CO and optionally further DME is formed. All DME formed during steps (a) and (b) is separated from the remaining gaseous mixture. Step (c) thus affords at least two products, the first being a gaseous mixture comprising synthesis gas and other components originating step (b) and substantially no DME, and the second being DME or a mixture comprising DME.

In one embodiment, step (b) is performed directly following step (a), without any significant further alterations to the gaseous mixture originating from step (a). In one embodiment, step (c) is performed directly following step (b), without any significant further alterations to the gaseous mixture originating from step (b). In one embodiment, step (a) is performed directly following step (c), without any significant further alterations to the gaseous mixture comprising synthesis gas originating from step (c). In one embodiment, step (a) is performed directly on the feedstock, without any significant alterations to the feedstock. In one embodiment, step (b) is performed directly on the feedstock, without any significant alterations to the feedstock. In one embodiment, step (b) is performed directly on the gaseous mixture consisting of the feedstock and the gaseous mixture originating from step (a), without any significant alterations to the gaseous mixture. Herein, "without any significant further alteration" refers to alterations in the composition of the gaseous mixture in question. As will be appreciated by the skilled person, (minor) changes in temperature and pressure are not considered significant alterations.

In one embodiment, the process according to the invention does not comprise a step wherein $CO_x$ is separated from DME, wherein x>1.4. In one embodiment, the process according to the invention does not comprise a step wherein $CO_2$ is separated from DME. In an especially preferred embodiment, the process according to the invention does not comprise a step where $CO_2$ is converted into CO in the recycle between step (c) and step (a) via (autothermal) reforming, i.e. the recycle between step (c) and step (a) preferably does not comprise an (autothermal) reforming step.

Feedstock

For the purpose of the present invention, it is important to distinguish the feedstock, i.e. the incoming mixture of reactants, which is introduced into the system or process according to the invention, and the feed of step (b). The latter is also referred to as a gaseous mixture which is subjected to step (b), and the molar ratio of $H_2$ to $CO_x$ therein is crucial for the present invention. In the gaseous mixture which is subjected to step (b), the molar ratio of $H_2$ to $CO_x$ should be at least (x+0.8). The molar ratio of $H_2$ to $CO_x$ in the feedstock should thus be chosen such that the feed of step (b) has the required $H_2$ to $CO_x$ molar ratio. The process according to the invention preferably further comprises a step wherein the composition of the recycle, i.e. the gaseous mixture originating comprising synthesis gas originating from step (c), or the gaseous mixture originating from step (a) is determined, such that the composition of the feedstock, in particular the amount of $H_2$ included therein, can be tuned towards an optimal composition of the feed of step (b). Such determining of a gaseous composition and such tuning of the composition of the feedstock are known to the skilled person. Preferably, the composition of the recycle is determined.

The feedstock for the production of DME according to the invention comprises at least $H_2$ and $CO_x$, wherein x=1-2. Compared to conventional DME production processes and facilities, which require CO as starting material and cannot use $CO_2$, the system according to the invention provides increased flexibility, as DME is produced from either CO, $CO_2$ or mixtures thereof. In other words, DME is readily produced with any value of x in the range 1-2. In the context of the present invention, the mixture of $H_2$ and $CO_x$, in any ratio and any possible value of x, is also referred to as "synthesis gas". The feedstock is thus a synthesis gas or contains a synthesis gas. In addition to the synthesis gas, the feedstock may optionally contain further components, such as methane and higher hydrocarbons, inert gases such as nitrogen, argon and the like.

$CO_x$ denotes CO, $CO_2$ or mixtures thereof, and may also be referred to as "carbon oxide", with CO and $CO_2$ being the two carbon oxide species, or as "CO and/or $CO_2$". The value of x denotes the number of oxygen atoms present per carbon atom in the carbon oxide fraction (i.e. $CO+CO_2$) of the feedstock, irrespective of any further oxygen and/or carbon atoms that may be present in the feedstock. Thus, x is in the range of 1-2, wherein x=1 indicates pure CO and x=2 indicates pure $CO_2$. An intermediate value for x indicates that a mixture of CO and $CO_2$ is present in the feedstock, which can readily be determined by the skilled person. As example, when x=1.9, 1.9 oxygen atoms are present per carbon atom, meaning that the molar ratio of $CO:CO_2$ is 1:9. Likewise, when x=1.5, the $CO:CO_2$ molar ratio is 1:1.

The process according to the invention operates efficiently using a feedstock wherein x is any value in the range 1-2. In one embodiment, the feedstock contains $CO_2$, or in other words x>1, i.e. 1<x≤2. The process and system according to the invention is particularly advantageous because $CO_2$ can be used as source of carbon atoms for the production of DME. Preferably, x>1.2, more preferably x>1.5, more preferably x>1.7. In one particularly preferred embodiment, x is close to 2, e.g. 1.8-2, or 1.9-2 or even about 2, or in other words the feedstock contains $CO_2$ and is substantially free from CO. In case substantial amounts of $CO_2$ are present in the feedstock, it is preferred that the feedstock is subjected to the reverse water gas shift reaction of step (b), in order to increase the CO content. Thus, when the feedstock is $CO_2$-rich, i.e. x=1.9-2 or x>1.5 or even x>1.2, the feedstock is preferably fed to step (b). In an alternative embodiment, the feedstock contains CO, or even CO is the major carbon oxide species and x is close to 1, e.g. 1-1.5, 1-1.2, or 1-1.1 or even about 1, and a reverse water gas shift reaction zone prior to a DME production zone is not required, and the feedstock may be introduced in step (a) or (b), without affecting the efficacy of the process. Thus, irrespective of the value of x, the feedstock is effectively introduced in step (b), but when CO is the major carbon oxide species, e.g. x=1-1.2, introduction in step (a) is also feasible without jeopardizing process efficacy. Thus, in a preferred embodiment, the feedstock is introduced in step (b).

The optimal molar ratio of $H_2$ to $CO_x$ in the feedstock depends mainly on the value of x. Theoretically, based on the stoichiometry of the reaction, the optimal $H_2$ to $CO_x$ molar ratio ranges from 1-2 when x=1 to 2-3 when x=2, depending on which reaction scheme is followed. One mole of $H_2$ is consumed when one mole of $CO_2$ is converted into one mole of CO and one mole of $H_2O$. In other words, a molar ratio of $H_2$ to $CO_x$ in the range of x to (x+1), wherein x=1-2, is theoretically favourable. For DME formation via reaction (5) or (6), the theoretically optimal $H_2$ to $CO_x$ molar ratio is (x+1). Although stoichiometric amounts of $H_2$ and $CO_x$ are preferred, the process according to the invention also runs smoothly with super-stoichiometric and even slight sub-stoichiometric amounts of $H_2$. Hence, the molar ratio of $H_2$ to $CO_x$ in the feedstock according to the invention is typically at least (x+0.8), preferably at least (x+1). The maximal $H_2$ content is not restricted from a technical standpoint, but for sake of efficiency the $H_2$ content typically does not exceed (x+10), or even (x+5), or even (x+2). Preferred ranges for the molar ratio of $H_2$ to $CO_x$ are thus (x+0.8) to (x+10), (x+1) to (x+10), (x+0.8) to (x+5), (x+1) to (x+5), (x+0.8) to (x+2) and (x+1) to (x+2). The process according to the invention operates smoothly with feedstocks having a broad range of $H_2$ to $CO_x$ molar ratios, as defined herein, which thus provides increased flexibility in the feedstock, compared to conventional processes for the production of DME. Greater excesses of $H_2$ over $CO_x$ have however not been found to be associated with further advantages and would only lead to significant accumulation of $H_2$ in the system. Excess $H_2$ could be removed from the system by a purge step, which is preferably implemented in the recycle between step (c) and step (a). Thus, in one embodiment, the process according to the invention comprises a step wherein $H_2$ is purged from the system, preferably the gaseous mixture comprising synthesis gas originating from step (c) is purged. Such purging of a recycle is known in the art. The purged gas may e.g. be used as fuel in a furnace or the like.

Although significant accumulation of $H_2$ in the system is preferably prevented, a slight excess of $H_2$ may be preferred as step (b) operates most optimally with an excess $H_2$, as discussed further below. The optimal molar ratio of $H_2$ to $CO_x$ in the feed of step (b) is about (x+2), which may be obtained by using a feedstock wherein the molar ratio of $H_2$ to $CO_x$ is slightly above stoichiometry, such as (x+1.01) to (x+2), preferably (x+1.1) to (x+1.2). Alternatively, the excess $H_2$ that is desired in step (b) is introduced in the reactor before the DME production is started or during an initial stage of the process. During the initial stage of the process, the feedstock has a $H_2$ to $CO_x$ molar ratio of (far) above (x+1), such as at least (x+1.5) or even at least (x+2).

In an alternative embodiment, not the $H_2$ to $CO_x$ molar ratio in the feed of step (b) is crucial, but the $H_2$ to $CO_x$ molar ratio in the feedstock is. In this embodiment, preferred ranges for the molar ratio of $H_2$ to $CO_x$ are thus (x+0.8) to (x+10), (x+1) to (x+10), (x+0.8) to (x+10), (x+0.8) to (x+5), (x+1) to (x+5), (x+0.8) to (x+2) and (x+1) to (x+2).

With the present invention, feedstocks for DME production become available that were never suitable for DME production, such as blast furnace gas (BFG), coke oven gas or even off-gases of carbon capture processes. Also more conventional feedstocks such as natural gas, SNG and coal or biomass gasification gases may be used, typically downstream a reforming step to increase the $H_2$ and CO content. If needed, additional $H_2$ can be added to such gases to arrive at the above defined molar ratios of $H_2$ to $CO_x$. Such tuning of the $H_2$ content based on the $CO_x$ content towards the stoichiometry of the reaction is known in the art. Thus, in a preferred embodiment, the feedstock originates at least in part from blast furnace gas (BFG), coke oven gas or a carbon capture processes. The flexibility in feedstock to be used in the synthesis of DME is a great improvement over prior art process for the production of DME.

In the process according to the invention, the feedstock as defined above can be introduced in step (a) or in step (b). Herein, "introduced in step (a)" means that the feedstock is subjected to step (a), and thus that the feedstock is received by the DME reactor of step (a) or that the feedstock is first combined with the recycle from step (c), i.e. the with the gaseous mixture comprising synthesis gas, before it is introduced in the DME reactor. Likewise, "introduced in step (b)" means that the feedstock is subjected to step (b), and thus that the feedstock is received by the reverse water gas shift reactor of step (b) or that the feedstock is first combined with the gaseous mixture originating from step (a) before it is introduced in the reverse water gas shift reactor.

Step (a)

The recycle from step (c), i.e. the gaseous mixture comprising synthesis gas originating from step (c), is subjected in step (a) to DME synthesis, which involves contacting the gaseous mixture with a catalyst capable of converting synthesis gas to DME. In one embodiment as indicated above, the feedstock is also subjected to step (a), preferably after combining with the recycle from step (c), although both the recycle as the feedstock may also be introduced separately in step (a). As equilibrium reactions are involved, the concentration of DME in the incoming gaseous stream, i.e. the gaseous mixture originating from step (c), should be as low as possible. Implementation of separation step (c) is thus of great benefit for the process according to the invention, as this ensures that the recycle does not contain significant amounts of DME and comprises mainly synthesis gas and optionally methanol.

Step (a) involves contacting the gaseous mixture comprising synthesis gas originating from step (c) and optionally the feedstock with a catalyst system, which is typically comprised in a catalyst bed. The catalyst system is capable of converting synthesis gas to DME, and typically contains a direct DME catalyst system. The direct DME catalyst system is typically selected from a bifunctional DME synthesis catalyst or a combination of a methanol synthesis catalyst and a methanol dehydratation catalyst. Any direct DME catalyst system known in the art is suitable to be used in this respect. Suitable catalysts include alumina containing copper/zinc oxide based catalysts ($Cu$—$ZnO$—$Al_2O_3$), but other catalysts are also suitable. Step (a) typically operates at 100-500° C., preferably 200-400° C., and 10-200 bar, preferably 20-100 bar.

In a preferred embodiment, step (a) is performed in separation-enhanced mode, or in other words, step (a) is performed in a separation-enhanced DME synthesis (SEDMES) reaction zone. "Separation-enhanced" refers to the separation of one of the products from the equilibrium mixture, such that the equilibrium shifts towards the products. Thus for the DME synthesis of step (a), $H_2O$ is preferably separated from the equilibrium mixture, as this shifts reactions (1) and (3), or (6) towards the products methanol or DME. Suitable means to accomplish separation-enhancement include the use of selective membranes and selective adsorbents. For example, the DME synthesis of step (a) is performed in sorption-enhanced mode, wherein $H_2O$ is adsorbed onto a water-selective adsorbent. Alternative means to accomplish separation-enhancement involves the use of selective membranes, which are permeable for one of the products, preferably for $H_2O$. When $H_2O$ selectively permeates such a membrane, it is separated from the equilibrium mixture which thus shifts towards the products of the DME synthesis reactions. Preferably, step (a) is performed in sorption-enhanced mode and the catalyst system further comprises a water-selective adsorbent.

A SEDMES reaction zone contains a catalyst system comprising the direct DME catalyst system, which is capable of converting synthesis gas into DME, and means for separating water from the reaction mixture, typically in the form of an adsorbent selective for water or a water-selective membrane.

Any water-selective adsorbent known in the art that is capable to adsorb water but that hardly adsorbs DME and preferably also hardly adsorbs methanol is suitable in this respect. It is preferred that also $H_2$ and $CO_x$ are not adsorbed onto the adsorbent. In a preferred embodiment, the water-selective adsorbent is a porous material, preferably having an average pore diameter of at most 4 Å, such that the pores are capable of accommodating water molecules but no DME molecules. Suitable water-selective adsorbents include silica-based adsorbents, alumina-based adsorbents, and mixtures thereof, especially aluminosilicates such as zeolites, alkaline earth metal oxides (e.g. Ca, Mg, Ba), composites of metal halides, sulfates and phosphates confined in porous matrices, such as in aluminosilicates, graphite and clays. The skilled person finds further guidance in Yuan et al., *Renewable and Sustainable Energy Reviews*, 2016, 54, 761-776. In an especially preferred embodiment, the water-selective adsorbent is a zeolite, most preferably a zeolite having an average pore diameter of at most 4 Å. Such materials are selective for water adsorption. Preferably, the average pore diameter is in the range of 1-3 Å. Suitable zeolites are type A zeolites, preferably zeolite 3 A, zeolite 4 A and mixtures thereof. Zeolite 3 A, zeolite 4 A and mixtures thereof are especially preferred, since they are highly selective for the adsorption of water. When a water adsorbent with larger pores is used, such as zeolite ZSM-5, the selectivity for water adsorption decreases and other molecules such as methanol and DME may be adsorbed onto the adsorbent. Moreover, the inventors found that ZSM-5 does not exhibit significant sorption-enhancing capacity. As such, the DME yield of the process is decreased and the composition of adsorbed species is less uniform which hampers regeneration of the catalyst system. As will be understood by the skilled person, the catalyst system may contain further components that are inert in or that promote the production of DME at the process conditions, such as a carrier.

Any type of membrane that is known in the art to be selective for permeation of water molecules, while retaining the other gaseous molecules is suitable to be used in a SEDMES reaction zone. The skilled person may find guidance in e.g. Smitha et al., *J. Membr. Sci.* 2004, 241, 1, 1-21. Suitable membranes include polymeric membranes such as polyvinyl alcohol-based polymeric membranes, polyimide-based membranes and sulfonated polymeric membranes (e.g. SPEEK or nafion-based), zeolite membranes like zeolite A, ZSM-5 and mordenite, silicalite, (amorphous) silica membranes and organic-inorganic hybrid silica membranes.

Organic-inorganic hybrid silica membranes include HybSi membranes, known from e.g. Castricum et al. *J. Mater. Chem.* 2008, 18, 2150-2158 and Agirre Arisketa et al. *Sep. Purif. Technol.* 2014, 121, 2-12. The SEDMES reactor preferably employs an organic-inorganic hybrid silica membrane, known from e.g. WO 2007/081212, WO 2010/008283, WO 2013/066184 and WO 2014/025259, all of which are herein incorporated by reference in their entirety, and these membranes may be prepared as described therein. Such membranes are resistant to high temperatures and transmembrane pressures, and are thus especially suitable to be used. Higher temperatures and transmembrane pressures lead to larger fluxes which in turn improve the (cost) efficiency of the process according to the invention.

The catalyst system comprised in the SEDMES reaction zone is capable of catalysing reactions (1)-(3) as defined above and at the same time capable of adsorbing water. In view thereof, the equilibrium of reaction (2) is pushed towards the reactants CO and $H_2O$, which in turns enables the use of (substantial amounts of) $CO_2$ as carbon oxide species in the feedstock. Secondly, the equilibria of reactions (1) and (3) are pushed towards the products methanol and DME respectively. The $CO_2$ produced is converted into CO (and $H_2O$, which is adsorbed) by reaction (2). These effects of the water adsorbent effectuate that the overall "once through" yield of DME is greatly increased, meaning that the need of recycles is minimized. Moreover, the formation of $CO_2$ is suppressed, which avoids cumbersome separation between $CO_2$ and DME from the equilibrium mixture (e.g. in step (c)) and largely eliminates the $CO_2$ recycle, two of the most costly aspects of conventional DME production. The product mixture emerging from the SEDMES reaction zone contains mainly DME and some remaining synthesis gas, depending on the ratio of $H_2$ to $CO_x$ in the feedstock.

During step (a), the recycle originating from step (c), which comprises at least synthesis gas and optionally methanol, is converted into DME. Step (a) affords an equilibrium mixture that contains at least DME and $CO_2$, the two products of the overall DME synthesis reaction, and typically remaining $H_2$ and CO are also present in the equilibrium mixture as well as some methanol, any inert gaseous species that originate from the feedstock. In case reaction zone (a) is a conventional DME production zone and not a SEDMES reaction zone, the equilibrium mixture will also contain substantial amounts of $H_2O$. However, in case reaction zone (a) is a SEDMES reaction zone, the equilibria are pushed towards the formation of DME, and the equilibrium mixture of zone (a) contains mainly DME, CO and $H_2$. Instead of separating the DME from the other species in this equilibrium mixture, it is fed to step (b), where the DME and any methanol is untouched and $CO_2$ (and $H_2$) is converted into CO (and $H_2O$). DME is eventually separated during step (c). As such, cumbersome separation between DME and $CO_2$ is avoided.

Step (b)

In step (b), a gaseous mixture comprising the gaseous mixture originating from step (a) and optionally the feedstock, is subjected to a separation-enhanced reverse water gas shift reaction. The gaseous mixture that is subjected to step (b), also referred to as the feed of step (b), typically consists of the gaseous mixture originating from step (a) and optionally the feedstock. Hence, in one embodiment, the process according to the invention includes a step of combining the feedstock with the gaseous mixture originating from step (a) prior to subjecting the combined gaseous mixture to step (b).

The water gas shift reaction is well-known in the art, and concerns the following equilibrium: $H_2O+CO \leftrightarrow H_2+CO_2$. Depending on the conditions and the catalyst used, the equilibrium may be more to the product side ($H_2+CO_2$) or to the reactant side ($H_2O+CO$). For the reverse water gas shift reaction, the equilibrium is shifted to the reactant side and favours the formation of $H_2O$ and CO at the expense of $H_2$ and $CO_2$. The skilled person knows how to select conditions and catalysts to promote the reverse water gas shift reaction. Reverse water gas shift reaction zones and reactors for the same are known in the art. Thus, step (b) involves contacting the feedstock with a reverse water gas shift catalyst, i.e. a catalyst capable of catalysing or promoting the reverse water gas shift reaction. Step (b) typically operates above 150° C., preferably at 150-1000° C., preferably at 150-500° C., more preferably at 200-400° C., most preferably at 200-350° C. The pressure is typically above 4 bar, such as 10-80 bar, more preferably 22-40 bar. Advantageously, step (b) typically operates above 150° C., preferably at 200-1000° C., more preferably at 200-500° C., most preferably at 200-350° C., and above 4 bar, preferably 10-80 bar, most preferably 22-40 bar. The skilled person finds further guidance in Haije and Geerlings, *Environ. Sci. Technol.* 2011, 45, 8609-8610, and in EP0737648.

The feed of step (b) thus contains $H_2$ and $CO_x$, wherein the molar ratio of $H_2$ to $CO_x$ is at least (x+0.8), preferably at least (x+1), more preferably at least (x+1.5), most preferably at least (x+2). The inventors surprisingly found that the process runs most optimally when super-stoichiometric amounts of $H_2$ are present in the feed of step (b), though stoichiometric and even slight sub-stoichiometric amounts can also be used. The maximal $H_2$ content is not restricted from a technical standpoint, but for sake of efficiency the $H_2$ content typically does not exceed (x+10), or even (x+5). Preferred ranges for the molar ratio of $H_2$ to $CO_x$ in the feed of step (b) are thus (x+0.8) to (x+10), (x+1) to (x+10), (x+1.5) to (x+10), (x+2) to (x+10), (x+0.8) to (x+5), (x+1) to (x+5) and (x+2) to (x+5). Although super-stoichiometric amounts of $H_2$ are most favourable, the process according to the invention operates smoothly with a broad range of $H_2$ to $CO_x$ molar ratios, as defined herein, which thus provides increased flexibility in the feedstock, compared to conventional processes for the production of DME. The $H_2$ to $CO_x$ molar ratio in the feed of step (b) may be influenced by adjusting (or "tuning") the amount of $H_2$ present in the feedstock and optionally by adjusting the purge.

The reverse water gas shift of step (b) according to the invention is separation-enhanced. Separation-enhanced water gas shift and reverse water gas shift reactions are known in the art. "Separation-enhanced" refers to the separation of one of the products from the equilibrium mixture, such that the equilibrium shifts towards the products. For the reverse water gas shift of step (b), this means that that either $H_2O$ or CO, preferably $H_2O$, is separated from the equilibrium mixture. Suitable means to accomplish separation-enhancement include the use of selective membranes and selective adsorbents. For example, the reverse water gas shift of step (b) is performed in sorption-enhanced mode, wherein $H_2O$ is adsorbed onto a water-selective adsorbent and the equilibrium mixture emerging from step (b) contains mainly CO and $H_2$. Alternative means to accomplish separation-enhancement involves the use of selective membranes, which are permeable for one of the products, preferably for $H_2O$. When $H_2O$ selectively permeates such a membrane, it is separated from the equilibrium mixture which thus shifts towards the products of the reverse water gas shift reaction. Preferably, step (b) is performed in sorption-enhanced mode. Sorption-enhanced water gas shift and reverse water gas shift reactions are known in the art. For the sorption-enhanced reverse water gas shift reaction, a reverse water gas shift catalyst is combined with an adsorbent for selective adsorption of water, which activities may be combined in a single material. Such a reverse water gas shift reaction may also be referred to as "steam sorption-enhanced". Suitable reverse water gas shift catalyst systems that may be used for step (b) are known in the art and include LTS (low temperature shift) catalysts, MTS (medium temperature shift) catalysts, sour shift catalysts, alumina and noble metal based catalysts. Preferred catalysts are based on Cu, Zn, Fe, Co, Mo, Al, Mg, Pt, Rh, Au or mixtures thereof, and may be alkali-promoted, preferably K-promoted. In one embodiment, the catalyst for the reverse water gas shift reaction of step (b) is selected from Cu/Zn-oxide based catalyst, a CoMoS-based catalyst, a Pt-, Rh- or Au-based catalyst and a Zn-alumina catalyst. Since water is separated or removed from the equilibrium mixture during step (b), the reaction is pushed towards the formation of CO (and separated $H_2O$).

In an especially preferred embodiment, step (b) is a separation-enhanced DME synthesis (SEDMES) reaction. A SEDMES reaction zone comprises a catalyst system which contains a direct DME catalyst system as reverse water gas shift catalyst. A SEDMES reaction zone has reverse water gas shift capacity and can thus be used in step (b). Since the water gas shift reaction (2) is pushed towards the reactants, the catalyst system comprised in the SEDMES reaction zone has reverse water gas shift activity. Hence, the SEDMES reaction zone is suitable as reverse water gas shift reaction zone in step (b). Thus, in one embodiment, step (b) is performed in a SEDMES reaction zone and catalytic bed comprised therein comprises the direct DME catalyst system and water-selective adsorbent as described above. In this embodiment, step (a) is preferably performed in a conventional DME production zone, preferably for the direct synthesis of DME.

Step (b) is performed in a reaction zone or in a reactor, which contains the reverse water gas shift catalyst and means for separating $H_2O$ from the equilibrium mixture. Such means typically include a water-selective adsorbent or a water-selective membrane, preferably a water-selective adsorbent is used. In one embodiment, the reverse water gas shift catalyst is a direct DME catalyst system. In addition to the gaseous mixture originating from step (a), also the feedstock may be introduced into the reactor of step (b). Herein, the gaseous mixtures of the feedstock and the product mixture of step (a) are mixed and converted together, to form a single product mixture of step (b). Any $CO_2$ that is comprised in the gaseous mixture originating from step (a) and in the feedstock is converted to CO, prior to the separation of step (c).

As $CO_2$ is converted into CO during step (b), the value of x decreases. Since an equilibrium mixture emerges from step (b), the value of x may still be larger than 1, however x is typically in the range of 1-1.2 in the gaseous mixture originating from step (b). As $H_2O$ is removed from the gaseous mixture by virtue of the water-selective adsorbent, the composition of the gaseous mixture originating from step (b) is mainly determined by the $H_2$ to $CO_x$ ratio and the value of x in the feedstock. In case the reaction zone in which step (b) is performed is a SEDMES reaction zone, $CO_x$ and $H_2$ are in part converted to methanol and DME already during step (b). Nevertheless, the equilibrium mixture of step (b) contains substantial amounts of $CO_x$, $H_2$, optionally methanol and DME and any further (inert) species that may be present in the feedstock. In case step (b) involves a conventional separation-enhanced reverse water gas shift reaction, the equilibrium mixture will contain no methanol and DME, unless those would be fed to step (a).

In a preferred embodiment, at least one of step (a) and step (b) is performed in a sorption-enhanced DME synthesis (SEDMES) reaction zone as indicated above. In one embodiment, step (a) is performed in a SEDMES reaction zone. In one embodiment, step (b) is performed in a SEDMES reaction zone. In one embodiment, steps (a) and (b) are performed in a SEDMES reaction zone. It is highly preferred that step (b) is performed in a SEDMES reaction zone and step (a) is a conventional DME production zone or a SEDMES reaction zone. Most preferably, step (b) is performed in a SEDMES reaction zone and step (a) is a conventional DME production zone. Although in terms of theoretical DME yield, it may be advantageous to use SEDMES as the main DME production in step (a), slurry reactors, which are typically needed to cope with the large amount of heat formed during DME synthesis in step (a), are not compatible with adsorbents. Especially regeneration of the adsorbent may be problematic when this is comprised in a slurry reactor. Thus, to utilize the advantages of SEDMES and at the same time avoiding any issue with heat formation, it is preferred that step (a) is performed in a conventional DME production zone and step (b) in a SEDMES or separation-enhanced reverse water gas shift reaction zone.

Step (c)

The gaseous mixture originating from step (b) is subjected to DME/synthesis gas separation. Such separation is known in the art and separates the DME from the other components in the gaseous mixture originating from step (b), including synthesis gas. Thus, step (c) affords as first product a gaseous mixture comprising synthesis gas and DME as second product. Any means known in the art to separate DME from a gaseous mixture containing DME and synthesis is gas is suitable to be used as step (c). Step (c) is typically performed by flash evaporation, distillation or a combination thereof. Preferably at least flash evaporation is employed in step (c), as that efficiently separates volatile synthesis gas from less volatile DME. In case the DME obtained as such contains further components, such as methanol and/or water, the less volatile fraction containing DME may be subjected to further separation. In a preferred embodiment, step (c) involves a series of (c1) flash evaporation and (c2) distillation. In the flash evaporation of (c1) all most volatile components are removed, including $H_2$ and $CO_x$ (i.e. synthesis gas), typically together with permanent (inert) gases that may be present. The remaining components are subjected to distillation, wherein DME is collected as top fraction from a distillation column and methanol as bottom fraction, optionally together with traces of water. The gaseous mixture comprising synthesis gas originating from step (c), typically originating form flash evaporation, is recycled to step (a). In case a separate stream of methanol is obtained in step (c), such as in step (c2), this may be discharged from the system as a by-product and used as deemed fit, or it may also be fed to step (a) to be converted into DME. The DME originating from step (c), typically from step (c2), is the main product from the process according to the invention.

The gaseous mixture comprising synthesis gas that originates from step (c) is recycled to step (a). This mixture contains, typically consists essentially of, $H_2$ and $CO_x$, and optionally (inert) permanent gases that are present in the gaseous mixture originating from step (b). Herein, x is typically 1-1.4, preferably 1-1.1, most preferably about 1, meaning that the $CO_2$ content is very low to negligible. In view thereof, the separation of step (c) is facilitated and no conversion of $CO_2$ to CO prior to step (a) is needed.

The process according to the invention preferably further comprises a step of regenerating the catalyst system of any sorption-enhanced reaction zone employed, such as the SEDMES reaction zone(s). At a certain point in time, the adsorbent will be fully occupied with adsorbed water molecules that no further water adsorption is possible. At this point, the adsorbent is referred to as "loaded" with water molecules. Regeneration of the adsorbent by drying (removal of water) enables reuse of the catalyst system for a further cycle of DME synthesis. The regeneration may be accomplished by any means known in the art for drying a solid adsorbent material. Suitable means include reducing the total pressure or the partial pressure of steam in the reactor (e.g. pressure swing adsorption (PSA) or vacuum pressure swing adsorption (VPSA)), increasing the temperature (e.g. temperature swing adsorption (TSA) mode), contacting the loaded adsorbent with a dry gas (e.g. passing a gas through the reactor), or combinations thereof. The dry gas should contain less than 0.1% water, and may comprise nitrogen, noble gases, hydrocarbons and even synthesis gas. Combinations of drying techniques, e.g. depressurisation and heating, may also be used. In this context, it is preferred that at least two SEDMES reactors are placed in parallel for performing a single step of each of (a) and/or (b) in the process according to the invention, such that one reactor may be regenerated while another reactor is being used for the production of DME. As such, continuous DME production is possible.

In case the SEDMES catalyst system contains the water-selective adsorbent as defined above as water-selective adsorbent, regeneration is facilitated compared to prior art DME production processes. In view of the small pores of the adsorbent, water will selectively adsorb thereon. Regeneration of the adsorbent will thus afford an effluent gas containing substantially pure steam. No further separation steps need to be performed on this effluent gas to extract valuable compounds such as methanol or even DME.

System

The invention further relates to an apparatus or system specifically designed to implement the process according to the invention. The system according to the invention is a modular system, in which at least three, preferably at least four modules are in fluid connection with each other. Herein, each module may be a separate unit or two or more modules may be integrated as a single unit. Preferably, each module is a separate unit and is distinguishable as such in the system. The modular system for performing the process according to the invention may also be referred to as DME synthesis facility or a DME production plant. The system according to the invention comprises:

(a) an inlet for receiving a feedstock comprising $H_2$ and $CO_x$, wherein x=1-2, (b) a reverse water gas shift reaction zone for converting $H_2$ and $CO_x$ to $H_2O$ and CO, comprising an inlet (b1) for receiving a gaseous mixture comprising the gaseous mixture originating from zone (d), wherein the molar ratio of $H_2$ to $CO_x$ in the gaseous mixture which is subjected to step (b) is at least (x+0.8), a catalyst bed (b2) comprising a separation-enhanced reverse water gas shift catalyst system, an outlet (b3) for discharging a gaseous mixture;

(c) a separator comprising an inlet (c1) for receiving the gaseous mixture originating from zone (b), means (c2) for separating the gaseous mixture in DME and a gaseous mixture comprising synthesis gas, an outlet (c3) for discharging the gaseous mixture comprising synthesis gas and an outlet (c4) for discharging DME; and (d) dimethyl ether production zone, comprising an inlet (d1) for receiving the gaseous mixture comprising synthesis gas originating from separator (c), a catalyst system (d2) capable of converting synthesis gas to DME and an outlet (d3) for discharging a gaseous mixture.

Herein, inlet (a) is in fluid connection with inlet (b1) or inlet (d1), outlet (b3) is in fluid connection with inlet (c1), outlet (c3) is in fluid connection with inlet (d1), and outlet (d3) is in fluid connection with inlet (b1).

First of all, the system according to the invention comprises an inlet (a) for receiving the feedstock. The system comprises at least two reaction zones, i.e. reaction zone (b) and reaction zone (d). The feedstock that is received via inlet (a) is led to reaction zone (b) or to reaction zone (d). Thus, inlet (a) is in fluid connection with inlet (b1) of reaction zone (b) or with inlet (d1) of reaction zone (d). Preferred locations of inlet (a) are in reaction zone (b), in reaction zone (b), in the fluid connection between reaction zone (d) and reaction zone (b), i.e. between outlet (d3) and inlet (b1), or in the fluid connection between separator (c) and reaction zone (d), i.e. between outlet (c3) and inlet (d1). In one embodiment, inlet (a) is located in reaction zone (b) or in the fluid connection between reaction zone (d) and reaction zone (b), preferably in the fluid connection between reaction zone (d) and reaction zone (b) (i.e. inlet (a) is in fluid connection with inlet (b1)). This embodiment corresponds to the process according to the invention wherein the feedstock is introduced in step (b). In an alternative embodiment, inlet (a) is located in reaction zone (d) or in the fluid connection between separator (c) and reaction zone (d), preferably in the fluid connection between separator (c) and reaction zone (d) (i.e. inlet (a) is in fluid connection with inlet (d1)). This embodiment corresponds to the process according to the invention wherein the feedstock is introduced in step (a). In an especially preferred embodiment, the system according to the invention contains two inlets, a first inlet (a1) and a second inlet (a2). Herein, inlet (a1) is located in reaction zone (b) or in the fluid connection between reaction zone (d) and reaction zone (b), preferably in the fluid connection between reaction zone (d) and reaction zone (b), and inlet (a2) is located in reaction zone (d) or in the fluid connection between separator (c) and reaction zone (d), preferably in the fluid connection between separator (c) and reaction zone (d). The system wherein both inlet (a1) and (a2) are present provides optimal flexibility in terms of feedstock composition and at the same time greatly simplifies DME production and thus reduces costs, compared to conventional DME production. Which inlet is used can be chosen depending on the composition of the feedstock. As discussed before, $CO_2$-rich feedstocks (i.e. x>1.5) are preferentially introduced in step (b) of the process according to the invention, and thus inlet (a1) is preferentially used. Likewise, CO-rich feedstocks (i.e. x<1.5) are preferentially introduced in step (a) of the process according to the invention, and thus inlet (a2) is preferentially used.

Reaction zone (b) is a separation-enhanced reverse water gas shift reaction zone and is designed for performing step (b) of the process according to the invention. Reverse water gas shift reaction zones and reactors for the same are known in the art. Reaction zone (b) is typically capable of operating above 150° C., preferably at 200-1000° C., most preferably at 200-500° C., and above 4 bar, preferably 10-80 bar.

Reaction zone (b) comprises an inlet (b1) for receiving the gaseous mixture originating from zone (d). In one embodiment, the feedstock is directly injected into reaction zone (b), and inlet (a) of the system is a further inlet of reaction zone (b). In an alternative embodiment, the feedstock is injected in the fluid connection between reaction zone (d) and reaction zone (b), i.e. between outlet (d3) and inlet (b1). As such, inlet (b1) is for receiving a mixture of the feedstock originating from inlet (a) and the gaseous mixture originating from zone (d). Reaction zone (b) further comprises a catalyst bed (b2), comprising a separation-enhanced reverse water gas shift catalyst system. Any catalyst system having reverse water gas shift activity as well as water separation activity known in the art may be used in bed (b2). Suitable reverse water gas shift catalyst systems are known in the art and are further defined above. The catalyst system further comprises means for separating $H_2O$ from the product mixture. The means for separating $H_2O$ from the product mixture may take the form of a water-selective adsorbent or a water-selective membrane. Suitable water-selective adsorbents and suitable water-selective membranes are known in the art and are further defined above. Reaction zone (b) further comprises at least one outlet (b3) for discharging a gaseous mixture comprising synthesis gas, which is in fluid connection with inlet (c1). Reaction zone (b) may contain a further outlet for discharging $H_2O$ that is desorbed from the adsorbent during regeneration or removed in the form of a membrane effluent. Typically, reaction zone (b) further comprises means for regenerating the adsorbent, which are capable of removing adsorbed $H_2O$ molecules from the adsorbent once it is loaded. Such means are known in the art.

The system according to the invention further comprises a separator (c), which is designed for performing step (c) of the process according to the invention. Separator (c) comprises an inlet (c1) for receiving the gaseous mixture originating from zone (b), means (c2) for separating the gaseous mixture in a first stream comprising synthesis gas and a second stream containing DME, an outlet (c3) for discharging to first stream and an outlet (c4) for discharging a second stream. An additional outlet (c5) may be provided for discharging a further stream of components that are removed from the DME, such as methanol and/or water. Suitable separators (c) are known in the art and include a flash evaporator, a distillation column or a combination thereof. The combination of flash evaporation and distillation is well-known in the art to isolate substantially pure DME from a product mixture. Outlet (c3) is in fluid connection with inlet (d1), such that the first stream can be led to zone (d). The second stream typically consists essentially of DME and is the main product of the process and system according to the invention.

Reaction zone (d) is a DME production zone and is designed for performing step (a) of the process according to the invention. Zone (d) may be a reaction zone for direct synthesis of DME or a reaction zone for indirect synthesis of DME. Such reaction zones and reactors for the same are known in the art. Reaction zone (d) may be for the direct synthesis of DME from synthesis gas, and thus contains one reactor comprising a direct DME catalyst system. Alternatively, reaction zone (d) may be for the indirect synthesis of DME from synthesis gas, and thus contains two reactors, one for the synthesis of methanol from synthesis gas, which comprises a methanol synthesis catalyst, and one for the dehydratation of method to form DME, which comprises a methanol dehydratation catalyst. Such reaction zones and reactor set-ups for the direct and the indirect synthesis of DME are known in the art, and are suitable to be used as reaction zone (d). In a preferred embodiment, reaction zone (d) is for the direct synthesis of DME from synthesis gas as described herein. Reaction zone (d) typically is capable of operating at 100-500° C., preferably 200-400° C., and 10-200 bar, preferably 50-100 bar.

Reaction zone (d) comprises an inlet (d1) for receiving the gaseous mixture comprising synthesis gas originating from reaction zone (c). Outlet (c3) is thus in fluid connection with inlet (d1). Reaction zone (d) further comprises one or more catalyst beds (d2), comprising a catalyst system for the production of DME from synthesis gas. Any catalyst system for the production of DME as known in the art may be used in bed(s) (d2). Suitable methanol synthesis catalysts that may be comprised in a first bed include alumina-based copper/zinc oxide catalysts ($Cu-ZnO-Al_2O_3$). Suitable methanol dehydratation catalysts that may be comprised in a second bed include $\gamma$-alumina and HZSM-5. Preferably, the methanol synthesis catalyst and the methanol dehydratation catalyst are provided in a single bed as a direct DME catalyst system, preferably a bifunctional catalyst. Preferred direct DME catalyst systems include Cu/ZnO/$\gamma$-alumina and Cu/ZnO/HZSM-5. Reaction zone (d) further comprises at least one outlet (d3) for discharging a gaseous mixture emerging from bed(s) (d2). This gaseous mixture comprises DME. Outlet (c3), and optionally outlet (c5), is in fluid connection with inlet (d1), and outlet (d3) is in fluid connection with inlet (b1).

The system according to the invention may further comprise a purge, typically a gas outlet, which is preferably located in the fluid connection between outlet (c3) and inlet (d1). Such a purge can be used to remove any excess $H_2$ and inert gases from the system, which may be present depending on the exact composition of the feedstock. Such purging is known in the art.

In an especially preferred embodiment, reaction zone (d) is not a SEDMES reaction zone and the equilibrium mixture of zone (d) comprises DME, methanol, $CO_xH_2$ and $H_2O$. DME is not isolated from this equilibrium mixture, but it is instead led to a SEDMES reaction zone (b). In case reaction zone (b) is a SEDMES reaction zone, the equilibrium mixture of zone (d) is conveniently led back to zone (b), wherein it is contacted with a SEDMES catalyst system as defined above. By subjecting the equilibrium mixture of zone (d) to SEDMES, the remaining $CO_2$ is converted to CO, which is in turn reacted with $H_2$ to form methanol and eventually DME. As water is adsorbed in the SEDMES reaction zone, the equilibria or reactions (1)-(3) are pushed towards $CO_2$ consumption and DME formation. If the stoichiometry between $H_2$ and $CO_x$ in the feedstock is carefully chosen, which is readily accomplished by tuning the amount of $H_2$ added to a carbon oxide species containing gas, e.g. to a $H_2$ to $CO_x$ molar ratio of at least x+1, DME is the main product of the process and system of the invention, and co-formed water ends up in adsorbed state onto the adsorbent. The equilibrium mixture emerging from step (b)/reactor (b) contains DME, $H_2$, $CO_x$, wherein x is close to 1, such as 1-1.2, and possibly some methanol. Separation in separator (c)/step (c) then involves separation into a first stream comprising $H_2$ and $CO_x$, a second stream consisting essentially of DME and optionally a third stream comprising methanol. The first and third stream are recycled to step (a)/reactor (d). No separation of DME from further gaseous components, such as $CO_2$, is needed. As especially the separation of DME from $CO_2$ is difficult, the process according to the embodiment is a marked improvement over the prior art. Also, the recycles of synthesis gas and methanol are much reduced in size compared to the recycles of synthesis gas, $CO_2$ and methanol that are needed in conventional DME production processes. A further key feature of the process according to this embodiment is that the large body of DME is produced in a conventional DME production zone (d), for which means are available to cope with extensive heat formation. Thus, zone (d) is advantageously equipped with means to cope with the heat produced therein, preferably zone (d) employs a slurry reactor.

Figure 1:
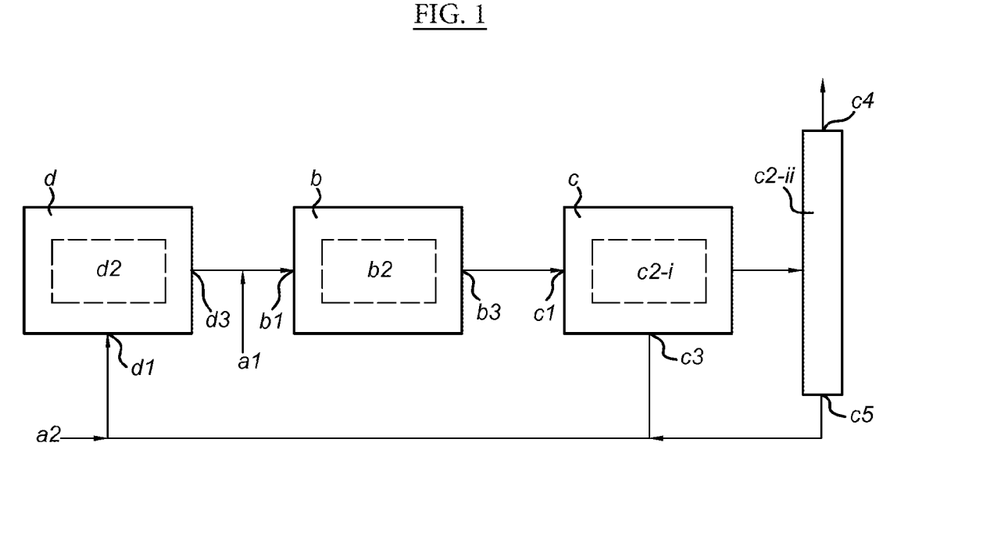
FIG. 1 is a schematic of a system in accordance with preferred embodiments of the invention described.

A first preferred system A is here described with reference to the FIGURE. The system according to this embodiment comprises a reaction zone (d), a reaction zone (b) downstream of zone (d), a separator (c) downstream of zone (b) and a recycle from separator (c) to reaction zone (d). Thus, outlet (d3) of reaction zone (d) is in fluid connection with inlet (b1) of reaction zone (b), outlet (b3) of reaction zone (b) is in fluid connection with inlet (c1) of separator (c) and outlets (c3) and (c5) of separator (c) are in fluid connection with inlet (d1) of reaction zone (d). Inlet (a) is located in the fluid connection between outlet (d3) and inlet (b1) and is indicated in the FIGURE as inlet (a1). In the system of the present embodiment, inlet (a2) is not necessarily present. As such, the feedstock is combined with the gaseous mixture originating from reaction zone (d) and the combined gaseous mixture is led through inlet (b1) to reaction zone (b). Alternatively, inlet (a) may be provided directly in reaction zone (b) as a separate inlet, wherein the combining with the gaseous mixture originating from reaction zone (d) occurs within reaction zone (b). In reaction zone (b), the CO content of the combined gaseous mixture is increased at the expense of $CO_2$ by bed (b2) comprising a reverse water gas shift catalyst. Reaction zone (b) is separation-enhanced, preferably sorption-enhanced, and thus contains means for achieving separation of $H_2O$, preferably wherein bed (b2) further comprises a water-selective adsorbent. The gaseous mixture, which has a reduced value for x, is then led via outlet (b3) to inlet (c1) of separator (c), which splits the gaseous mixture into a synthesis gas containing first stream that is led via outlet (c3) to reaction zone (d), a DME containing second stream that is discharged as product via outlet (c4) and a third stream that is led via outlet (c5) to reaction zone (d). Separator (c) further comprises means (c2-i) for separating the first stream containing synthesis gas from the remaining components in the gaseous mixture emerging from reaction zone (b) and means (c2-ii) separating the second stream containing mainly DME from remaining components originating from means (c2-i), which together form the third stream. Means (c2-i) is preferably a flash evaporator and means (c2-ii) is preferably a distillation column. Means (c2-i) is provided with an outlet (c3) for discharging the first stream. Means (c2-ii) is provided with an outlet (c4) for discharging DME and an outlet (c5) for discharging the remaining components. Outlets (c3) and (c5) are in fluid connection with inlet (d1) of reaction zone (d). The recycle from outlet (c3) to inlet (d1) preferably contains a purge. In reaction zone (d), the CO, $H_2$ and methanol present in the first and third streams are converted into DME, preferably via direct DME synthesis by catalyst system (d2). Reaction zone (d) further comprises an outlet (d3) for discharging the equilibrium mixture obtained in reaction zone (d), Outlet (d3) is in fluid connection with inlet (b1) of reaction zone (b). In a preferred aspect of this embodiment, reaction zone (b) is a SEDMES reaction zone as defined above.

A second preferred system B is identical to system A described above, except for the location of the inlet. Inlet (a) is provided in the fluid connection between outlets (c3) and (c5) and inlet (d1), indicated as inlet (a2) in the FIGURE.

Alternatively, inlet (a) may be provided directly in reaction zone (d) as a separate inlet, and is in fluid connection with inlet (d1). As such, the feedstock is first led through reaction zone (c) and is then led via the fluid connection between outlet (c3) and inlet (b1) to reaction zone (b).

Most preferred is system C, which is identical to systems A and B with the only exception that inlet (a1) (corresponding with system A) and inlet (a2) (corresponding with system B) are both present. Which inlet is used can be chosen depending on the composition of the feedstock. As discussed before, $CO_2$-rich feedstocks (i.e. x>1.5) are preferentially introduced in step (b) of the process according to the invention, and thus inlet (a1) is preferentially used. Likewise, CO-rich feedstocks (i.e. x<1.5) are preferentially introduced in step (a) of the process according to the invention, and thus inlet (a2) is preferentially used. System C combines all advantages of the process according to the invention as discussed herein in a reactor set-up and thus offers optimal flexibility in terms of feedstock composition and at the same time greatly simplifies DME production and thus reduces costs, compared to conventional DME production.

Example

The 0.2-0.4 mm sieve fraction of a catalyst system (10 g Cu/Zn-based water gas shift catalyst and 40 g zeolite-3 A adsorbent) was loaded into a SEDMES reactor. Six different feeds (see Table 1) were introduced at a flow of 260 sccm. During reaction/adsorption, the reactor operated in the temperature range of 225-275° C. at 25 bar(a). When complete saturation of the catalyst was observed ($H_2O$ breakthrough), the catalyst system was regenerated by switching to a nitrogen feed (at 25 bar(a)), then depressurizing to 1.7 bar(a) and subsequent heating to 400° C. When all $H_2O$ was removed from the adsorbent, the reactor was cooled and repressurized to reaction/adsorption conditions. $CH_4$ was added as inert component to represent the hydrodynamics of the reactor system.

TABLE 1

| | Feed compositions (in mol %) | | | | | |
|---|---|---|---|---|---|---|
| Feed | $N_2$ | $H_2$ | CO | $CO_2$ | $CH_4$ | x | $H_2/CO_x$ |
| 1 | 19.2 | 57.7 | 0.0 | 19.2 | 3.8 | 2 | 3.0 |
| 2 | 19.2 | 51.5 | 25.4 | 0.0 | 3.8 | 1 | 2.0 |
| 3 | 19.2 | 53.8 | 15.4 | 7.7 | 3.8 | 1.33 | 2.3 |
| 4 | 19.2 | 61.5 | 0.0 | 15.4 | 3.8 | 2 | 4.0 |
| 5 | 19.2 | 57.7 | 19.2 | 0.0 | 3.8 | 1 | 3.0 |
| 6 | 19.2 | 58.8 | 11.9 | 6.2 | 3.8 | 1.34 | 3.3 |

The composition of the mixture emerging from the SEDMES reactor during the adsorption/reaction phase was analysed by mass spectrometry and Infra-red spectrometry, and compared with the theoretical thermodynamic equilibrium mixtures (at T=275° C. and p=25 bar(a)). Table 2 below lists carbon selectivities (fraction of carbon atoms that ended up in a certain product) of the experimentally obtained sorption-enhanced equilibrium mixtures and the theoretical thermodynamic equilibrium mixtures, i.e. without sorption-enhancement.

TABLE 2

| Carbon selectivities (in mol %) of the product mixtures | | | | | | | | |
|---|---|---|---|---|---|---|---|---|
| | Thermodynamic equilibrium | | | | Sorption-enhanced equilibrium | | | |
| Feed | MeOH | DME | $CO_2$ | CO | MeOH | DME | $CO_2$ | CO |
| 1 | 1.9 | 4.4 | 78.6 | 15.1 | 1.9 | 67.1 | 1.5 | 29.5 |
| 2 | 1.9 | 50.9 | 23.4 | 23.7 | 2.1 | 63.8 | 1.8 | 32.3 |
| 3 | 2.5 | 31.0 | 43.2 | 23.2 | 2.1 | 68.5 | 1.9 | 27.5 |
| 4 | 2.5 | 5.9 | 75.2 | 16.4 | 2.3 | 76.3 | 1.2 | 20.2 |
| 5 | 2.7 | 52.9 | 22.7 | 21.7 | 2.5 | 81.2 | 1.2 | 15.0 |
| 6 | 3.1 | 32.3 | 42.0 | 22.6 | 2.5 | 80.3 | 0.8 | 16.4 |

Compared to the thermodynamic equilibria, carbon selectivities for DME are dramatically increased in the sorption-enhanced mode. Moreover, the carbon selectivity for $CO_2$ was drastically reduced, giving DME and CO as main products. The product mixtures of the sorption-enhanced reactions were very similar for all values of x in the range 1-2, confirming that the process according to the invention provides flexibility in terms of the carbon oxide species present in the feedstock. The thermodynamic equilibria show that hardly any DME is formed using $CO_2$, while even at x=1 (pure CO) the DME yield was still lower as in the sorption-enhanced mode. Increasing the $H_2$ content from $H_2:CO_x$=x+1 to x+2 further increases the carbon selectivity for DME and at the same time prolongs the adsorbent lifetime. The duration before complete saturation of the adsorbent was reached was increased for the feeds with $H_2:CO_x$=x+2, meaning that less frequent regeneration is needed and, since the feed flow was constant over time, more feedstock is converted to DME in a single cycle of the SEDMES reactor.

The invention claimed is:

1. A process for the synthesis of dimethyl ether (DME) from a feedstock comprising $H_2$ and $CO_x$, wherein x=1 or 2, comprising sequentially:
    (a) subjecting the gaseous mixture comprising synthesis gas from step (c) to DME synthesis by contacting the gaseous mixture with a catalyst capable of converting synthesis gas to DME to obtain a gaseous mixture comprising DME;
    (b) subjecting a gaseous mixture comprising the gaseous mixture from step (a) to a separation-enhanced reverse water gas shift reaction; and
    (c) subjecting the gaseous mixture from step (b) to DME/synthesis gas separation to obtain DME and a gaseous mixture comprising synthesis gas, which is recycled to step (a),
    wherein the feedstock is introduced in step (a) or step (b) and wherein the molar ratio of $H_2$ to $CO_x$ in the gaseous mixture which is subjected to step (b) is at least (x+0.8).

2. The process according to claim 1, wherein the feedstock comprises $CO_x$, wherein x is 1.5-2 and the feedstock is introduced in step (b).

3. The process according to claim 2, wherein the feedstock comprises $CO_x$, wherein x is 1.9-2 and the feedstock is introduced in step (b).

4. The process according to claim 1, wherein the feedstock comprises $CO_x$, wherein x is 1-1.5 and the feedstock is introduced in step (a).

5. The process according to claim 4, wherein the feedstock comprises $CO_x$, wherein x is 1-1.2 and the feedstock is introduced in step (a).

6. The process according to claim 1, wherein the molar ratio of $H_2$ to $CO_x$ in the feedstock is in the range of (x+1) to (x+10).

7. The process according to claim 1, wherein step (a) and/or step (b) is performed in a separation-enhanced DME synthesis (SEDMES) reaction zone.

8. The process according to claim 7, wherein the SEDMES reaction zone is sorption-enhanced and comprises a catalyst system which contains a direct DME catalyst system and a water-selective adsorbent.

9. The process according to claim 8, wherein the water-selective adsorbent is a zeolite.

10. The process according to claim 9, wherein the zeolite has an average pore diameter of at most 4 Å.

11. The process according to claim 8, wherein step (a) is performed in a SEDMES reaction zone comprising a catalyst system which contains a direct DME catalyst system and a water-selective adsorbent.

12. The process according to claim 1, wherein step (a) is performed in a direct DME synthesis reaction zone, comprising a catalyst system which contains a direct DME catalyst system and no water-selective adsorbent.

13. The process according to claim 1, wherein the gaseous mixture originating from step (b) is separated in step (c) in DME and a gaseous mixture comprising synthesis gas and wherein the synthesis gas consists of $H_2$ and $CO_x$, wherein x=1-1.4.

14. The process according to claim 13, wherein the gaseous mixture originating from step (b) is separated in step (c) in DME and a gaseous mixture comprising synthesis gas and wherein the synthesis gas consists of $H_2$ and $CO_x$, wherein x=1-1.1.

15. The process according to claim 1, wherein the direct DME catalyst system is a bifunctional DME synthesis catalyst or a combination of a methanol synthesis catalyst and a methanol dehydration catalyst.

* * * * *